United States Patent [19]
Scott et al.

[11] Patent Number: 5,763,707
[45] Date of Patent: Jun. 9, 1998

[54] PRODUCTION OF PENTAFLUOROETHANE

[75] Inventors: John David Scott, Near Northwich; Michael John Watson, Long Newton; Paul Nicholas Ewing, Warrington, all of United Kingdom

[73] Assignee: Imperial Chemical Industries PLC, United Kingdom

[21] Appl. No.: 716,369

[22] PCT Filed: Apr. 4, 1995

[86] PCT No.: PCT/GB95/00766

§ 371 Date: Sep. 19, 1996

§ 102(e) Date: Sep. 19, 1996

[87] PCT Pub. No.: WO95/27688

PCT Pub. Date: Oct. 19, 1995

[30] Foreign Application Priority Data

Apr. 6, 1994 [GB] United Kingdom .................. 9406813

[51] Int. Cl.⁶ ...................................... C07C 17/08
[52] U.S. Cl. ...................... 570/168; 570/167; 570/166; 570/169
[58] Field of Search ........................... 570/166, 167, 570/168, 169

[56] References Cited

FOREIGN PATENT DOCUMENTS 0502605  9/1992  European Pat. Off. .
9216482  10/1992  WIPO .

*Primary Examiner*—Alan Siegel

[57] ABSTRACT

There is provided a process for the production of pentafluoroethane which comprises contacting a hydrofluorochloroethane having the formula: $C_2H_1Cl_{1+x}F_{1+y}$ wherein x and y are each independently 0,1,2 or 3 provided x+y is 3 with hydrogen fluoride in the vapor phase and in the presence of a fluorination catalyst which comprises zinc or a compound of zinc and chromia, chromium fluoride or chromium oxyfluoride.

9 Claims, No Drawings

PRODUCTION OF PENTAFLUOROETHANE

This application is a 371 of PCT/GB95/00766 filed on Apr.4, 1995.

This invention relates to a process for the production of pentafluoroethane.

According to the present invention there is provided a process for the production of pentafluoroethane which comprises contacting a hydrofluorochloroethane having the formula:

$$C_2H_1Cl_{1+x}F_{1+y}$$

wherein x and y are each independently 0, 1, 2 or 3 provided that x+y is 3, with hydrogen fluoride in the vapor phase and in the presence of a fluorination catalyst which comprises zinc or a compound of zinc and chromia, chromium fluoride or chromium oxyfluoride.

We have found that use of this particular catalyst for the fluorination of the defined hydrochlorofluoroethanes provides for highly selective production of pentafluoroethane with minimal formation of chlorofluorocarbons, in particular chloropentafluoroethane.

Preferred compositions, methods of preparation, methods of regeneration and forms of the catalyst are described in our published European Application No 502, 605, the contents of which are incorporated herein by reference.

The temperature at which the process is effected may be in the range from about 200° to about 450° C., preferably from about 300° C. to about 450° C. and especially from about 350° C. to about 450° C. Atmospheric, subatmospheric or superatmospheric pressures mat be employed, although to aid throughput of vapours thorough the equipment we prefer top employ superatmospheric pressure, say a superatmospheric pressure up to about 30 barg, and particularly a pressure on the range from about 5 barg to about 20 barg.

The relative proportion of hydrogen fluoride to starting compound of formula $$C_2H_1Cl_{1+x}F_{1+y}$$

wherein x and y are each independently 0, 1, 2 or 3 provided that x+y is 3 (hereafter referred to as the starting compound), may vary within wide limits although we generally prefer to employ a stoichiometric molar excess of hydrogen fluoride. The molar ratio of hydrogen fluoride to starting compound will therefore usually be greater than about 2:1 and we prefer to employ a molar ratio of hydrogen fluoride to starting compound in the range from about 2:1 to about 20:1 and preferably in the range from about 5:1 to about 15;1, especially in the range from about 5:1 to about 10:1.

Preferably the feed to the process of the invention is substantially free of hydrogen chloride. Thus, the process of the invention is preferably effected with a feed to the process comprising less than 10 mole % hydrogen chloride, especially less than 5 mole % hydrogen chloride.

The starting composition for the process of the present invention may be a single compound of formula $C_2H_1Cl_{1+x}F_{1+y}$, for example chlorotetrafluoroethane, dichlorotrifluoroethane or trichlorodifluoroethane although usually the starting composition will comprise a composition of two or more and even a composition comprising all of the starting compounds of formula $C_2H_1Cl_{1+x}F_{1+y}$ since the starting composition for the process of the present invention is conveniently produced itself by the vapour phase catalytic reaction of perchloroethylene with hydrogen fluoride to form a composition which usually comprises amounts of most or even all of the hydrochlorofluoroethanes of formula $C_2H_1Cl_{1+x}F_{1+y}$.

According to a preferred embodiment of the invention there is provided a process for the production of pentafluoroethane which comprises (i) contacting perchloroethylene with hydrogen fluoride in the vapour phase in the presence of a fluorination catalyst whereby to form a product stream comprising a hydrochlorofluoroethane of formula $C_2H_1Cl_{1+x}F_{1+y}$ wherein x and y are each independently 0, 1, 2 or 3 provided that x+y is 3, and (ii) contacting the product stream from step (i) with hydrogen fluoride in the vapour phase and in the presence of a fluorination catalyst comprising zinc and/or nickel or a compound of zinc and/or nickel and chromia, chromium fluoride or chromium oxyfluoride whereby to produce pentafluoroethane.

The temperature at which step (i) is effected may be in the range from about 150° C. to about 350° C., preferably from about 180° C. to about 320° C. and especially from about 200° C. to about 300° C. Atmospheric, subatmospheric or superatmospheric pressures mat be employed, although to aid throughput of vapours through the equipment we prefer to employ superatmospheric pressure, say a superatmospheric pressure up to about 30 barg, and particularly a pressure in the range from about 5 barg to about 20 barg.

The relative proportion of hydrogen fluoride to perchloroethylene may vary within wide limits although we generally prefer to employ a stoichiometric molar excess of hydrogen fluoride. The molar ratio of hydrogen fluoride to perchloroethylene will therefore usually be greater than about 3:1, preferably greater than 5:1 and we prefer to employ a molar ratio of hydrogen fluoride to perchloroethylene in the range from about 5:1 to about 20:1 and preferably in the range from about 7:1 to about 15:1, especially in the range from about 7:1 to about 12:1.

The catalyst employed in steps (i) and (ii) may be the same or different so that the two step process may be effected, if desired, in a single reaction vessel over a single catalyst bed comprising zinc or a compound of zinc and chromia, chromium fluoride or chromium oxyfluoride whereby to produce pentafluoroethane.

However, in this preferred embodiment of the invention we have further found that different catalysts are preferable for steps (i) and (ii) of the process. Thus, it is preferred to employ a catalyst having a high activity (per pass conversion) for the conversion of perchloroethylene in step (i) of the process whilst it is important to employ a catalyst which demonstrates a high selectivity for the production of pentafluoroethane from the hydrochlorofluoroethanes in step (ii).

According to a second aspect of the invention there is provided a process for the production of pentafluoroethane which comprises (i) contacting perchloroethylene with hydrogen fluoride in the vapour phase in the presence of a first fluorination catalyst whereby to form a product stream comprising a hydrochlorofluoroethane of formula $C_2H_1Cl_{1+x}F_{1+y}$ wherein x and y are each independently 0, 1, 2 or 3 provided that x+y is 3, and (ii) contacting the product stream from step (i) with hydrogen fluoride in the vapour phase and in the presence of a second fluorination catalyst which is different from the first fluorination catalyst whereby to produce pentafluoroethane.

Preferably a catalyst as defined for the process of the first aspect of the invention is employed in step (ii) of the process since we have found this catalyst to have a substantially higher selectivity for the production of pentafluoroethane from the defined hydrochlorofluoroethanes than any other catalyst we have tried.

The catalyst employed in step (i) of the process however may be any known fluorination catalyst which has a high activity for the conversion of perchloroethylene to hydrochlorofluoroethanes, for example catalysts based upon alumina or aluminium fluoride and which may also comprise one or more metals, for example nickel, cobalt, iron etc. We particularly prefer to employ a chromia catalyst in step (i) since this catalyst has a substantially higher per pass conversion of perchloroethylene to hydrochlorofluoroethanes under comparable conditions than that of a catalyst comprising zinc or a compound of zinc and chromia.

The catalysts for step (i) and (ii) of the process may be present in different reaction zones of the same reactor vessel or they may each be carried in a separate reactor vessel. By a "reaction zone" there is meant a zone or region containing a catalyst under certain conditions of temperature and pressure and by different reaction zones there is meant zones or regions at different temperatures.

As described previously, it is preferable that hydrogen chloride is substantially absent in step (ii) of the process. Hydrogen chloride is produced as a substantial by-product from step (i) of the process and according to a further aspect of the invention there is provided a process for the production of pentafluoroethane which comprises (i) contacting perchloroethylene with hydrogen fluoride in the vapour phase in the presence of a fluorination catalyst whereby to form a product stream comprising a hydrochlorofluoroethane of formula $C_2H_1Cl_{1+x}F_{1+y}$ wherein x and y are each independently 0, 1, 2 or 3 provided that x+y is 3, and hydrogen chloride, (A) separating hydrogen chloride from the product stream from step (i) and (ii) contacting the product stream from step (A) with hydrogen fluoride in the vapour phase in the presence of a fluorination catalyst whereby to produce pentafluoroethane.

Removal of hydrogen chloride from the product stream from step (i) in step (A) may be conveniently effected by distilling the product stream from step (i) and recovering a bottoms product comprising hydrogen chloride and a tops stream comprising the organic components of the product stream from step (i) and hydrogen fluoride. This product stream may then be fed to step (ii).

The process is preferably operated on a continuous basis in which make up perchloroethylene and hydrogen fluoride are fed to step (i) and additional hydrogen fluoride may, if required be fed to step (ii).

The product stream from step (ii) may be purified so as to recover pentafluoroethane. Any unreacted hydrochlorofluoroethanes of formula $C_2H_1Cl_{1+x}F_{1+y}$ may be recycled to step (i) or step (ii) of the process.

In a further preferred embodiment, the product steam from step (ii) is passed over a fluorination catalyst heated to low temperatures, for example a temperature in the range from about 80° C. to about 200° C. in order to convert any unsaturated impurities present to saturated hydrochlorofluoroethanes which may, as described above be recycled to step (i) or (ii) of the process.

Furthermore, any chloropentafluoroethane present in the pentafluoroethane recovered from the process may be removed by contacting the contaminated pentafluoroethane with hydrogen in the vapour phase and in the presence of a hydrogenation catalyst, for example a catalyst comprising palladium supported on active carbon, as is described in our published International Application No. WO94/02439.

In embodiments of/or aspects of the invention where the catalyst for step (i) and the catalyst for step (ii) are carried in separate reaction vessels, then the two reaction vessels (hereafter "reactors") may be arranged in parallel or in series.

In embodiments in which the step (i) and step (ii) reactors are arranged in series, the product stream from one of the step (i) or (ii) reaction vessels is passed to the other vessel and the product steam of this other reaction vessel is fed to a purification system in which step (A) is effected. Thus, the product stream from the step (i) reactor may be passed to the step (ii) reactor and the product steam from the step (ii) reactor may be fed to a purification system in which step (A) is effected. Alternatively, the product stream from the step (i) reactor may be passed to the purification system in which step (A) is effected and one or more streams from the purification system comprising unreacted starting materials and compounds of formula $C_2HCl_{x+1}F_{y+1}$ may be passed to the step (ii) reactor. The product stream from the step (ii) reactor may be passed to the step (i) reactor.

However, as already described it is also preferable that hydrogen chloride is substantially removed before step (ii) of the process. Hydrogen chloride is produced as a substantial by-product from step (i) of the process and we prefer therefore that the product stream from the step (i) reactor is fed to the purification system in which step (ii) is effected and the product stream from the step (ii) reactor is passed to the step (i) reactor.

In embodiments in which the step (i) and step (ii) reaction vessels are arranged in parallel, the product streams from the reactors are preferably fed to a common purification system in which step (A) is effected and from which pentafluoroethane is recovered, unconverted perchloroethylene is recycled to the step (i) reaction vessel and unconverted compounds of formula $C_2HCl_{x+1}F_{y+1}$ are recycled to the step (ii) reaction vessel.

In step (A) the stream fed to the purification system in a series or parallel reactors embodiments typically comprises compounds of formula $C_2HCl_{x+1}F_{y+1}$, in particular dichlorotrifluoroethanes and chlorotetrafluoroethanes, trichlorotrifluoroethanes and diclorotetrafluoroethanes, pentafluoroethane, chloropentafluoroethane, unreacted hydrogen fluoride and perchloroethylene, by-product hydrogen chloride and small amounts of other by-products, for example, 1,1,1-trifluoro-2-chloroethane and 1,1,1,2-tetrafluoroethane.

This stream may be fed, for example, to a purification system which comprises a first distillation column from which hydrogen fluoride, dichlorotrifluoroethane [HCFC 123/123a] and other heavies are removed as a bottom fraction whilst the remainder of the stream is removed as a top fraction. The bottom fraction from this first column may be recycled to the reactor or to one or both of the reactors.

The top fraction from the first column, after aqueous scrubbing and drying if desired in order to remove the acid components, hydrogen chloride and hydrogen fluoride, may be fed to a second distillation column from which pentafluoroethane [HFA 125] is withdrawn together with chloropentafluoroethane [CFC 115] as a top fraction whilst the remainder of the stream, comprising mainly chlorotetrafluoroethane [HCFC 124/124a], chlorotrifluoroethane [HCFC 133/133a], tetrafluoroethane [HFA 134/134a] and dichlorotetrafluoroethane [CFC 114/114a] is withdrawn as a bottom fraction. The pentafluoroethane containing chloropentafluoroethane withdrawn as a top fraction may be further treated to effect purification of the pentafluoroethane as described hereinbefore.

The bottom fraction from the second column may be fed to a third distillation column from which tetrafluoroethane [HFA 134/134a] is withdrawn as a top fraction whilst the remainder of the stream is withdrawn as a bottom fraction and passed to a fourth distillation column from which chlorotetrafluoroethane [HCFC 124/124a] is withdrawn as a top fraction whilst dichlorotetrafluoroethane [CFC 114/114a] and chlorotrifluoroethane [HCFC 133/133a] are withdrawn as a bottom fraction. The chlorotetrafluoroethane [HCFC 124/124a] may be recycled to a reactor for fluorination to pentafluoroethane [HFA 125]. The bottom fraction from the fourth column is usually disposed of, for instance by thermal oxidation.

The purification system employed preferably comprises a first distillation column in which unreacted perchloroethylene and unconverted compounds of formula $C_2HCl_{x+1}F_{y+1}$ in which x is 1, 2 or 3, are separated (as a bottoms stream) from the other components (as a tops stream) and recycled to the step (i) reactor, and at least one further distillation column by which pentafluoroethane is separated from the other components of the tops stream and recovered and chlorotetrafluoroethane is separated from dichlorotetrafluoroethane and recycled.

The tops stream from the first distillation column is preferably treated in order to remove at least hydrogen chloride. In particular the tops steam from the first distillation column may be scrubbed with water to remove hydrogen fluoride and hydrogen chloride before being fed to the at least one further distillation column. However, in this case the hydrogen fluoride in the tops stream is also removed, resulting in a lower hydrogen fluoride efficiency for the process. Alternatively, the tops stream from the first distillation column may itself be distilled in order to separate a tops stream comprising hydrogen chloride, pentafluoroethane and chloropentafluoroethane from a bottoms stream comprising the other components. This bottoms stream may then be fed to the at least one further distillation column, whilst the tops stream may be fed to a distillation column in order to recover pentafluoroethane from the tops stream.

Where aqueous scrubbing is employed to remove hydrogen chloride and hydrogen fluoride, the at least one further distillation column preferably comprises two distillation columns in which in the first further column pentafluoroethane is separated from chlorotetrafluoroethane and dichlorotetrafluoroethane and in the second column chlorotetrafluoroethane is separated from chlorotetrafluoroethane. Where distillation is employed to separate hydrogen chloride from the tops stream from the first distillation column, the at least one further distillation column need only comprise one distillation column in which chlorotetrafluoroethane is separated from dichlorotetrafluoroethane.

Furthermore in those embodiments of/or aspects of the invention in which two reactor vessels are employed, we have also found that we are able to employ for at least one of the reactors an "adiabatic" reactor, that is a reactor to which none, or little, thermal regulation, i.e. heating or cooling, is required. Indeed, where desired, it is possible that both reactors may be adiabatic. In these circumstances, we generally prefer to employ an adiabatic reactor for the reactor in which step (ii) of the process is effected, that is the hydrofluorination of a compound of formula $C_2H_1Cl_{1+x}F_{1+y}$, and more preferably that both reactors are adiabatic.

The invention is illustrated but not limited by the following examples.

EXAMPLE 1

15 g of a chromia catalyst having a particle size of 2.0 to 3.4mm was charged to a ½ inch internal diameter Inconel reactor tube and hydrogen fluoride was passed over the catalyst at 380° C. and a pressure of 3 barg for 16 hours. The temperature was then lowered to 350° C., the pressure was increased to 10 barg and hydrogen fluoride and perchloroethylene were passed over the catalyst at a molar ratio of hydrogen fluoride to organic of 6:1, giving a contact time of 30 seconds. The reactor off-gases were sampled, scrubbed to remove acids and analysed by Gas Chromatography. The results are shown in Table 1.

From the results, the yield of pentafluoroethane was 18% and the selectivity to pentafluoroethane and hydrochlorofluoroethanes of formula $CH_1Cl_{1+x}F_{1+y}$ was 88%.

EXAMPLE 2

The procedure of example 1 was repeated except that the catalyst employed comprised 8% (by weight of the catalyst) zinc and chromia. The catalyst was prepared by co-precipitating zinc hydroxide and chromium hydroxide from a solution of zinc nitrate and chromium ((III) nitrate, and then calcining the hydroxides.

The results for this catalyst are also shown in Table 1.

TABLE 1

| OFF-GAS COMPOSITION. | EXAMPLE. | |
|---|---|---|
| (mole %) | 1 | 2 |
| $C_2F_5H$ | 17 | 18 |
| $C_2F_4ClH$ | 32 | 14 |
| $C_2F_3Cl_2H$ | 35 | 55 |
| $C_2F_2Cl_3H$ | 2 | <1 |
| $C_2F_3ClH_2$ | 2 | 10 |
| $C_2F_5Cl$ | 0.1 | 3 |
| $C_2Cl_4$ | 11 | <1 |

EXAMPLE 3

The procedure of example 2 was repeated except that hydrogen fluoride and $C_2F_3Cl_2H$ were passed over the catalyst using a molar ratio of hydrogen fluoride to organic of 5:1. The conversion of $C_2F_3Cl_2H$ was 80% and the selectivity to pentafluoroethane and chlorotetrafluoroethane was 99.2%.

EXAMPLE 4

The procedure of example 1 was repeated except that hydrogen fluoride and FC-123 were passed over the catalyst using a molar ratio of hydrogen fluoride to organic of 8.5:1. The conversion of FC-123 at 320° C. was 100% and the selectivity to FC-125 and FC-124 was 96.2%. CFC-115 levels were 1.4%.

EXAMPLE 5

The same catalyst as in example 2 was tested at a pressure of 10 barg and a molar ratio of hydrogen fluoride to perchloroethylene of 5:1, giving a contact time of 55 seconds. Over the temperature range 270°–310° C., the following results were obtained:

| Off Gas Composition (mole %) | | | | | | |
|---|---|---|---|---|---|---|
| Temp (°C.) | FC-125 | FC-124 | FC-123 | FC-122 | FC-133a | Per |
| 270 | <1 | 1.2 | 29 | 32.1 | 0.3 | 33.7 |
| 280 | <1 | 3 | 39.6 | 23.9 | 0.4 | 30.1 |
| 290 | <1 | 7 | 49.8 | 15.1 | 0.6 | 24.6 |

-continued

| Temp (°C.) | FC-125 | FC-124 | FC-123 | FC-122 | FC-133a | Per |
|---|---|---|---|---|---|---|
| 300 | 1 | 12.3 | 53.1 | 9.4 | 0.8 | 20.9 |
| 310 | 3.6 | 21.8 | 52.6 | 4.6 | 1.2 | 14.3 |

We claim:

1. A process for the production of pentafluoroethane which comprises (i) contacting perchloroethylene with hydrogen fluoride in the vapour phase in the presence of a first fluorination catalyst whereby to form a product stream comprising a hydrochlorofluoroethane of formula $C_2H_1Cl_{1+x}F_{1+y}$ wherein x and y are each independently 0, 1, 2 or 3 provided that x+y is 3 and (ii) contacting the product stream from step (i) with hydrogen fluoride in the vapour phase in the presence of a second fluorination catalyst comprising zinc and/or nickel or a compound of zinc and/or nickel and chromia, chromium fluoride or chromium oxyfluoride whereby to produce pentafluoroethane.

2. A process as claimed in claim 1 in which the temperature in step (ii) is in the range from 200° C. to 450° C.

3. A process as claimed in claim 1 in which the pressure is in the range from 5 barg to 20 barg.

4. A process as claimed in claim 1 in which the step (i) is effected at a temperature in the range from 150° C. to 350° C.

5. A process as claimed in claim 1 in which the molar ratio of hydrogen fluoride to perchloroethylene is in the range from 5:1 to 20:1.

6. A process for the production of pentafluoroethane as claimed in claim 1 wherein the second fluorination catalyst is different from the first fluorination catalyst.

7. A process as claimed in claim 6 in which in step (i) the catalyst comprises chromia.

8. A process for the production of pentafluoroethane as claimed in claim 1 which comprises the step of (A) separating hydrogen chloride from the product stream from step (i) prior to carrying out step (ii).

9. A process as claimed in claim 1 in which the molar ratio of hydrogen fluoride to halocarbon in step (ii) is in the range from about 2:1 to about 20:1.

* * * * *